US012172977B2

United States Patent
Are et al.

(10) Patent No.: US 12,172,977 B2
(45) Date of Patent: Dec. 24, 2024

(54) 2,2-DIMETHYL-N-[6-(1-METHYL-PIPERIDIN-4-CARBONYL)-PYRIDIN-2-YL]-PROPIONAMIDE, METHOD FOR PREPARING (6-AMINO-PYRIDIN-2-YL)-(1-METHYL-PIPERIDIN-4-YL)-METHANONE USING SAID COMPOUND, AND USE OF SAID COMPOUND IN THE PREPARATION OF LASMIDITAN

(71) Applicant: Moehs Ibérica, S.L., Rubí-Barcelona (ES)

(72) Inventors: Celeste Are, Rubí— Barcelona (ES); Carles Sánchez Casals, Rubí—Barcelona (ES); Alicia Dobarro Rodríguez, Rubí—Barcelona (ES)

(73) Assignee: Moehs Ibérica, S.L., Rubí—Barcelona (ES)

( * ) Notice: Subject to any disclaimer, the term of this patent is extended or adjusted under 35 U.S.C. 154(b) by 592 days.

(21) Appl. No.: 17/618,960

(22) PCT Filed: Jun. 30, 2020

(86) PCT No.: PCT/EP2020/068358
§ 371 (c)(1),
(2) Date: Dec. 14, 2021

(87) PCT Pub. No.: WO2021/001350
PCT Pub. Date: Jan. 7, 2021

(65) Prior Publication Data
US 2022/0306601 A1   Sep. 29, 2022

(30) Foreign Application Priority Data
Jul. 1, 2019   (ES) ..................... 01930607

(51) Int. Cl.
*C07D 401/06*   (2006.01)
(52) U.S. Cl.
CPC ................... *C07D 401/06* (2013.01)
(58) Field of Classification Search
CPC .................................................... C07D 401/06
See application file for complete search history.

(56) References Cited

U.S. PATENT DOCUMENTS

| | | | |
|---|---|---|---|
| 2001/0051727 A1 | 12/2001 | Maligres et al. | |
| 2004/0199024 A1 | 10/2004 | Mackewitz et al. | |

FOREIGN PATENT DOCUMENTS

| | | | |
|---|---|---|---|
| CN | 110981854 | * | 4/2020 |
| CN | 110981854 A | | 4/2020 |
| IN | 2019/11015218 | | 8/2021 |
| IN | 2019/11027190 | | 8/2021 |
| IN | 201911029132 A | | 8/2021 |
| IN | 201911032679 A | | 8/2021 |
| WO | WO 2003/084949 | | 10/2003 |
| WO | WO 2011/123654 | | 10/2011 |
| WO | WO 2018/010345 | | 1/2018 |

OTHER PUBLICATIONS

Capi et al., Lasmiditan for the treatment of migraine. Expert Opin Investig Drugs. Feb. 2017;26(2):227-234.
Goadsby et al., Migraine—current understanding and treatment. N Engl J Med. Jan. 24, 2002;346(4):257-70.
Mase et al., Synthesis of a muscarinic receptor antagonist via a diastereoselective Michael reaction, selective deoxyfluorination and aromatic metal-halogen exchange reaction. J Org Chem. Oct. 5, 2001;66(20):6775-86.
Schuster et al., New strategies for the treatment and prevention of primary headache disorders. Nat Rev Neurol. Oct. 27, 2016;12(11):635-650.

* cited by examiner

*Primary Examiner* — D Margaret M Seaman
(74) *Attorney, Agent, or Firm* — Casimir Jones, SC; Tristan A. Fuierer

(57) ABSTRACT

The present invention relates to a new intermediate, (2,2-dimethyl-N-[6-(1-methyl-piperidin-4-carbonyl)-pyridin-2-yl]-propanamide) useful in the synthesis of lasmiditan, to a method for obtaining same, to the use of said intermediate for preparing lasmiditan, to a method for preparing lasmiditan making use of said intermediate, and to a method for preparing an intermediate ((6-amino-pyridin-2-yl)-(1-methyl-piperidin-4-yl)-methanone) from (2,2-dimethyl-N-[6-(1-methyl-piperidin-4-carbonyl)-pyridin-2-yl]-propanamide).

14 Claims, 3 Drawing Sheets

2,2-DIMETHYL-N-[6-(1-METHYL-PIPERIDIN-4-CARBONYL)-PYRIDIN-2-YL]-PROPIONAMIDE, METHOD FOR PREPARING (6-AMINO-PYRIDIN-2-YL)-(1-METHYL-PIPERIDIN-4-YL)-METHANONE USING SAID COMPOUND, AND USE OF SAID COMPOUND IN THE PREPARATION OF LASMIDITAN

CROSS-REFERENCE TO RELATED APPLICATIONS

This application is filed under the provisions of 35 U.S.C. § 371 and claims the priority of International Patent Application No. PCT/EP2020/068358 filed on 30 Jun. 2020 entitled "2,2-DIMETHYL-N-[6-(1-METHYL-PIPERIDIN-4-CARBONYL)-PYRIDIN-2-YL]-PROPIONAMIDE, METHOD FOR PREPARING (6-AMINO-PYRIDIN-2-YL)-(1-METHYL-PIPERIDIN-4-YL)-METHANONE USING SAID COMPOUND, AND USE OF SAID COMPOUND IN THE PREPARATION OF LASMIDITAN" in the name of Celeste ARE, et al., which claims priority to Spanish Patent Application No. P201930607, filed on 1 Jul. 2019, both of which are hereby incorporated by reference herein in their entirety.

FIELD OF THE INVENTION

The present invention relates to a new intermediate useful in the synthesis of lasmiditan, to a method for obtaining same, to the use of said intermediate for preparing lasmiditan, and to a method for preparing lasmiditan making use of said intermediate.

BACKGROUND OF THE INVENTION

Primary headache disorders, including migraine, are among the most common diseases and the main causes of disability around the world. Migraine affects more than 14% of adults worldwide. Treatment options available for migraine have unsatisfactory levels of efficacy, tolerability, and patient compliance. In the 2013 "Global Burden of Disease Study", migraine represented more than half of all the years lost to disability attributed to neurological disorders (New strategies for the treatment and prevention of primary headache disorders, N. M. Schuster & A. M. Rapoport, Nature Reviews Neurology (2016) 12, 635-650). Migraine is typically characterized by severe headache attacks lasting from 1 to 3 days, associated with nausea, vomiting, photophobia, and phonophobia (migraine without aura), and in one third of the patients, neurological aura symptoms (migraine with aura) (Goadsby, P J et al., New England Journal of Medicine 2002; 346: 257-270).

Lasmiditan, 2,4,6-trifluoro-N-[6-(1-methyl-piperidin-4-ylcarbonyl)-pyridin-2-yl]-benzamide of formula (I), is a highly potent selective agonist of the 5-HT$_{1F}$ receptor which is being developed for the treatment of migraine (see, for example, Lasmiditan for the Treatment of Migraine, Capi, M. et al., Expert Opinion Investigational Drugs, (2017), Vol. 26, No. 2, 227-234).

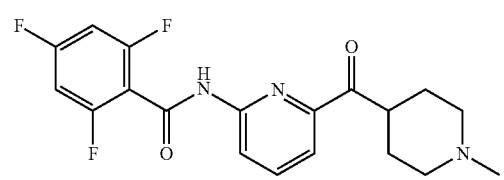

(I)

International patent application WO 03/084949 A1 describes lasmiditan as well as two methods for the preparation thereof.

Method 1

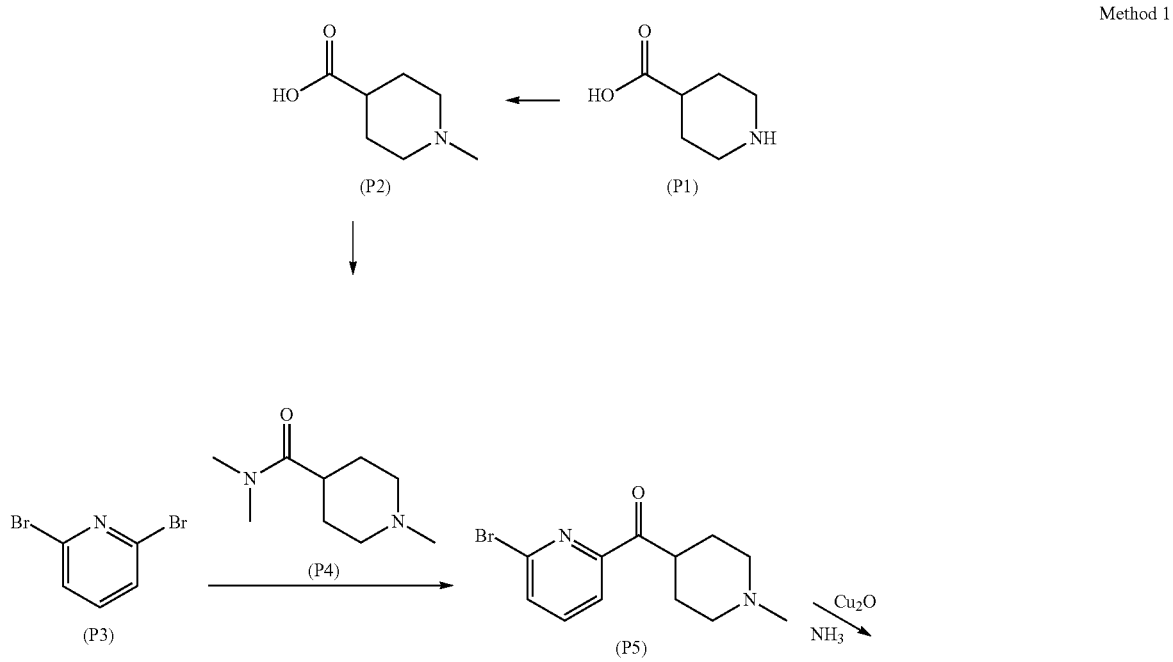

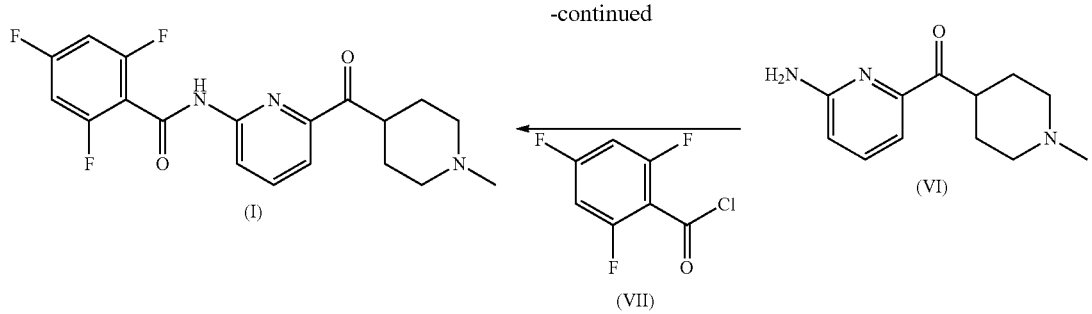

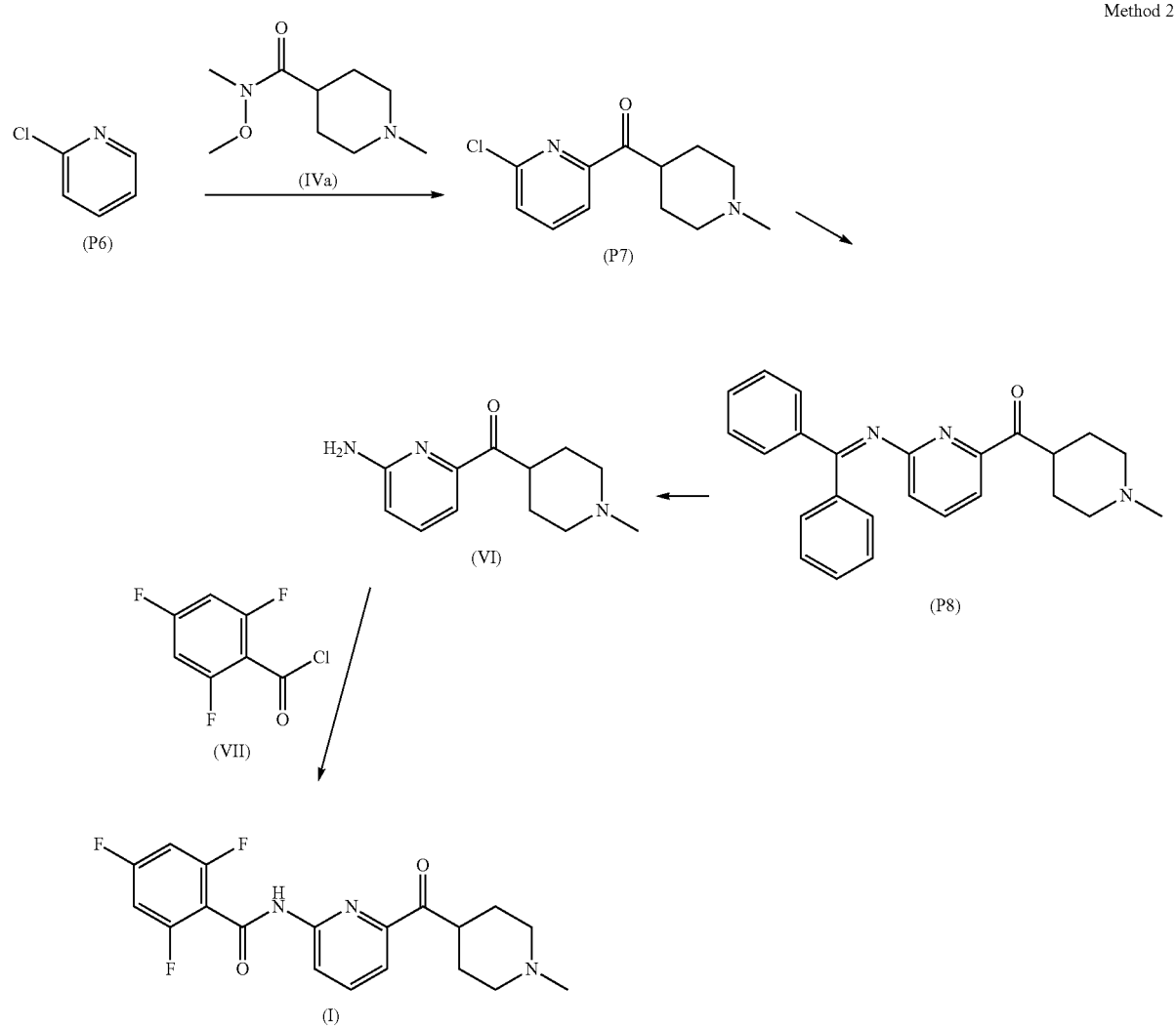

As explained in said patent application (page 26, paragraph 1), the use of intermediate (P4) as in method 1 has advantages over the use of intermediate (IVa) used in method 2 because (P4) is not hygroscopic and furthermore allows obtaining higher yields and greater chemoselectivity in the condensation reaction of said intermediates with the corresponding halopyridines (P3) or (P6) than those obtained with (IVa).

Furthermore, method 2 involves one more reaction step than method 1. Therefore, method 1 seems to be the preferred method, which is confirmed as it is the only one of the two methods claimed in the application.

As shown in Example 21 and preparations 3 to 7 of said application, method 1 proceeds with a yield of 43.4%.

An alternative method for preparing lasmiditan is described in international patent application WO 2011/123654 A1.

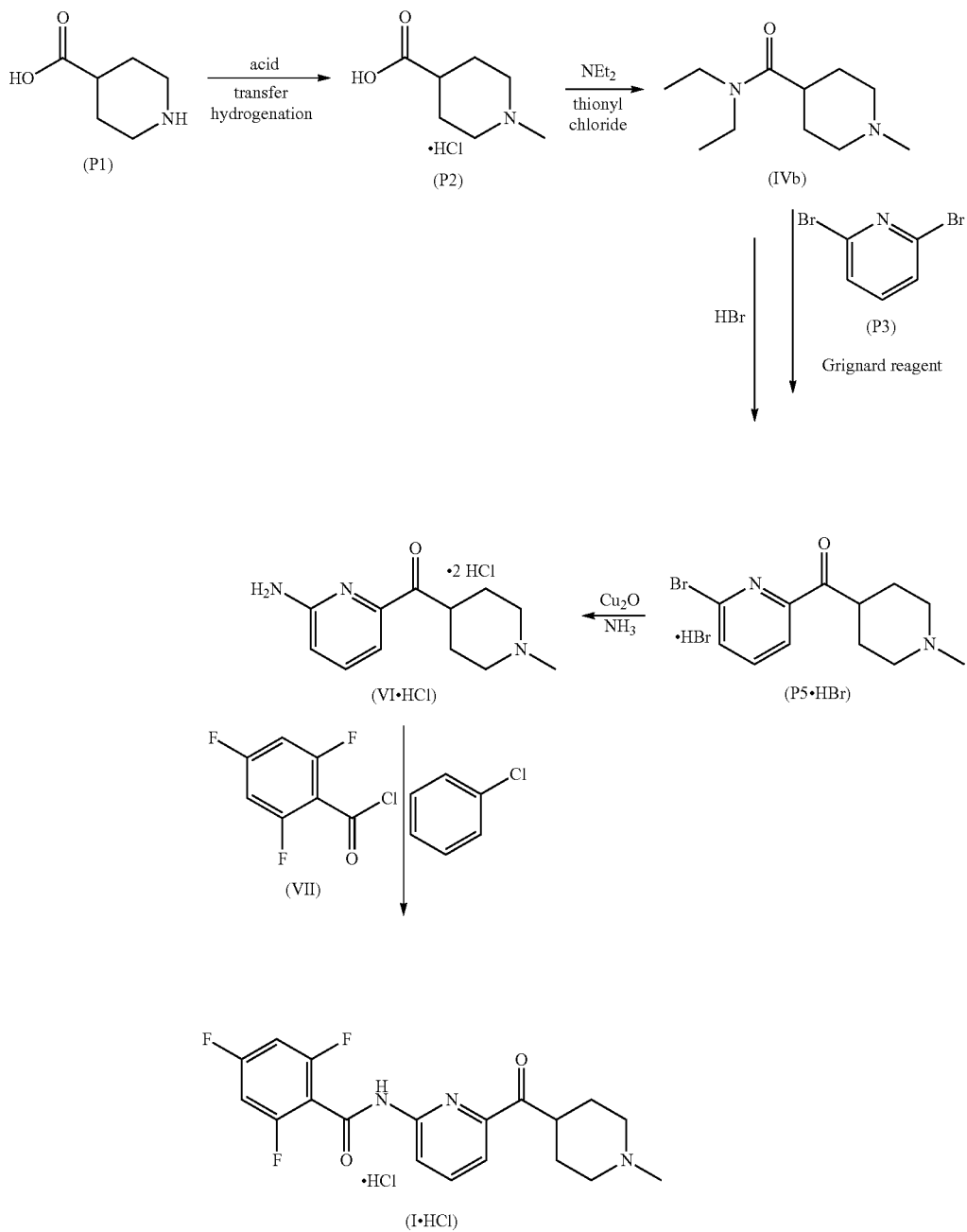

As shown in Example 2 of said application, the method takes place with a yield of 31.6%.

All the methods of the state of the art take place by means of the preparation of intermediate (VI) [(6-amino-pyridin-2-yl)-(1-methyl-piperidin-4-yl)-methanone], either in the form of a free base or hydrochloride salt, and the subsequent condensation thereof with intermediate (VII).

Therefore, there is a need in the state of the art for alternative methods for the synthesis of lasmiditan, as well as intermediate (VI) [(6-amino-pyridin-2-yl)-(1-methyl-piperidin-4-yl)-methanone], which present improvements with respect to those already existing methods, for example improvements in terms of yield, purity, and/or the possibility of isolating the intermediates as crystalline products that can be readily filtered.

SUMMARY OF THE INVENTION

The inventors have discovered a new method for a more efficient synthesis of (6-amino-pyridin-2-yl)-(1-methyl-piperidin-4-yl)-methanone (intermediate (VI)), which enables an efficient synthesis of lasmiditan as shown in the following scheme:

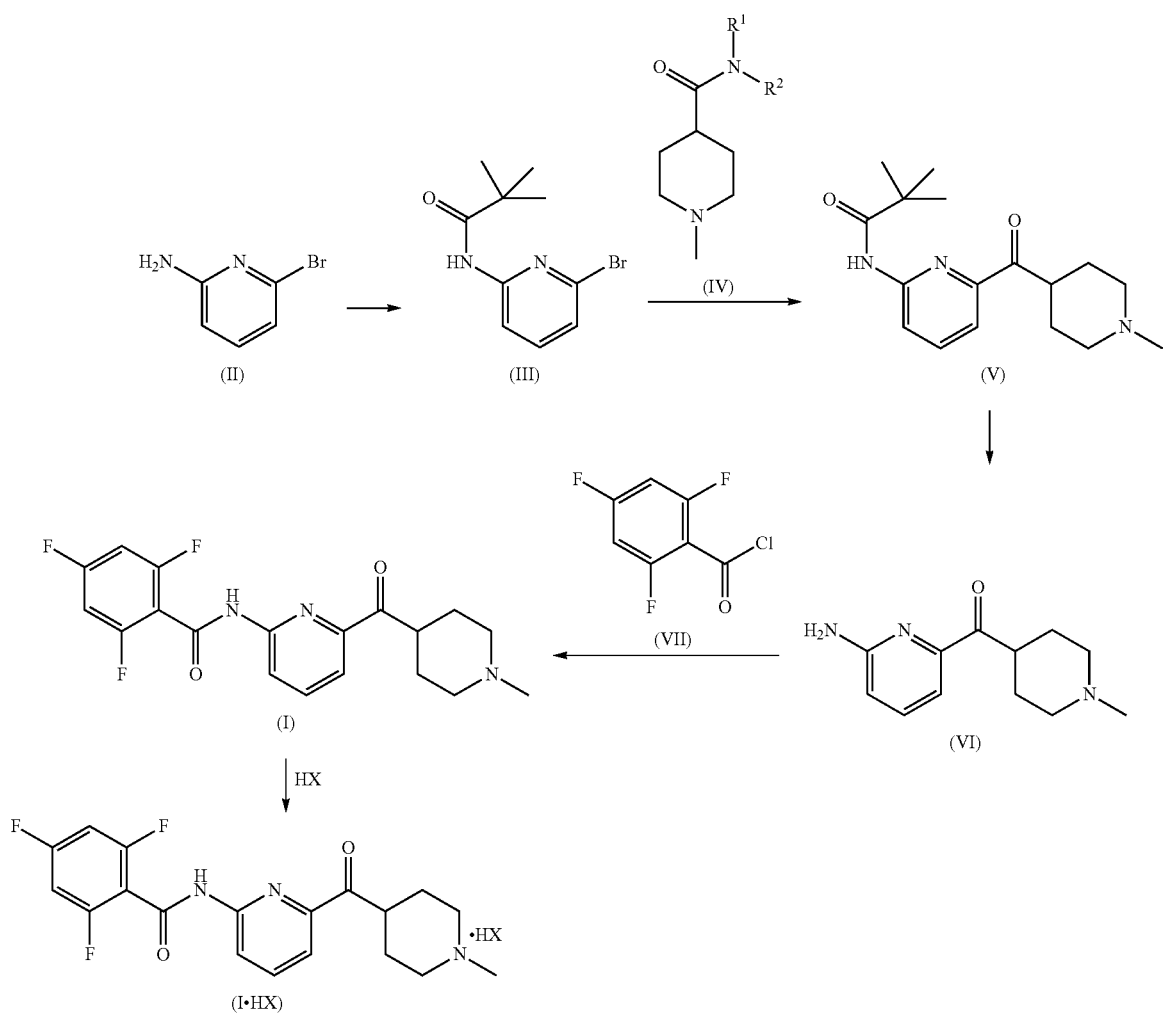

DETAILED DESCRIPTION OF THE INVENTION

In a first aspect, the present invention relates to the compound 2,2-dimethyl-N-[6-(1-methyl-piperidin-4-carbonyl)-pyridin-2-yl]-propionamide (V) or to a salt thereof which is useful in the preparation of intermediate (VI) which can be used for preparing lasmiditan (I) or the salts thereof (I•HX). Preferably, the compound of formula (V) is used in the form of a free base.

When used in the form of a salt, the addition salts of an organic or inorganic acid, such as benzenesulfonic acid, p-toluenesulfonic acid, methylsulfonic acid, succinic acid, oxalic acid, maleic acid, and the like, among organic acids, or hydrochloric acid, hydrobromic acid, sulfuric acid, or phosphoric acid and the like, among inorganic acids, are particularly suitable.

In an embodiment of the first aspect, the present invention relates to a compound (V) characterized by presenting a heat/temperature curve in a differential scanning calorimetry (DSC) having a negative peak at a temperature comprised between 125 and 140° C., preferably 134.21±3° C.

In a second aspect, the present invention relates to a method of preparing (6-amino-pyridin-2-yl)-(1-methyl-piperidin-4-yl)-methanone (VI) or a salt thereof which comprises reacting 2,2-dimethyl-N-[6-(1-methyl-piperidin-4-carbonyl)-pyridin-2-yl]-propionamide (V) with an acid, and eventually, converting the resulting salt into the free base. The compound (V) can be used in the form of its corresponding salt, so the release of the salt must first be performed. The addition salts of an organic or inorganic acid, such as benzenesulfonic acid, p-toluenesulfonic acid, methylsulfonic acid, succinic acid, oxalic acid, maleic acid, and the like, among organic acids, or hydrochloric acid, hydrobromic acid, sulfuric acid, or phosphoric acid and the like, among inorganic acids, can be mentioned by way of example among the salts of compound (V).

In one embodiment, the preceding reaction is carried out by dissolving 2,2-dimethyl-N-[6-(1-methylpiperidin-4-carbonyl)-2-pyridyl]propanamide (V) in water and adding an acid, such as a concentrated hydrochloric acid, to said solution, keeping the mixture under stirring for 2 to 4 hours, preferably 3 hours at the reflux temperature.

After keeping under stirring, an aqueous solution of a base, such as a saturated NaHCO₃ solution is added until a pH between about 6 and 8, preferably about 8, is added and an extraction is performed with several fractions of ethyl acetate. Alternatively, the aqueous solution of a base may be a 30% solution of NaOH, which is added until a pH of about 12 is obtained, and extraction is performed with several fractions of ethyl acetate. The solvent of the combined organic phases is eliminated by means of distillation to obtain a residue comprising (6-amino-2-pyridyl)-(1-methyl-4-piperidyl)methanone (VI) which is used without further purification in the next reaction.

In an embodiment of the second aspect of the invention, the acid used for reacting 2,2-dimethyl-N-[6-(1-methyl-piperidin-4-carbonyl)-pyridin-2-yl]-propionamide (V) or a salt of said compound is hydrochloric acid.

In an embodiment of the second aspect of the invention, 2,2-dimethyl-N-[6-(1-methyl-piperidin-4-carbonyl)-pyridin-2-yl]-propionamide (V) or a salt thereof (as previously defined) are obtained by reacting N-(6-bromo-pyridin-2-yl)-2,2-dimethyl-propionamide (III) with a 1-methyl-piperidine-4-carboxylic acid amide of formula (IV) or the salts thereof

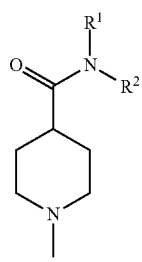
(IV)

wherein $R^1$ is selected from the group consisting of $C_1$-$C_3$ alkyl and $C_1$-$C_3$ alkoxy, and $R^2$ is selected from the group consisting of $C_1$-$C_3$ alkyl, or wherein $R^1$ and $R^2$ form, together with the nitrogen atom to which they are attached, a 5 to 6-membered heterocycle which may further comprise an oxygen atom, in the presence of an organolithium compound and, if a salt of 2,2-dimethyl-N-[6-(1-methyl-piperidin-4-carbonyl)-pyridin-2-yl]-propionamide (V) is to be obtained, reacting the obtained product with the corresponding acid. Preferably, the organolithium compound is selected from the group consisting of methyllithium, isopropyllithium, n-butyllithium, sec-butyllithium, tert-butyllithium, n-hexyllithium, and phenyllithium, preferably n-hexyllithium, n-butyllithium, and phenyllithium, or mixtures thereof. The addition salts of an organic or inorganic acid, such as benzenesulfonic acid, p-toluenesulfonic acid, methylsulfonic acid, succinic acid, oxalic acid, maleic acid, and the like, among organic acids, or hydrochloric acid, hydrobromic acid, sulfuric acid, or phosphoric acid and the like, among inorganic acids, can be mentioned by way of example among the salts of compound (IV).

In a more particular embodiment of the second aspect of the invention, in the amide of formula (IV) used, $R^1$ is selected from the group consisting of methyl and ethyl, and $R^2$ is selected from the group consisting of methoxy and ethyl, or wherein $R^1$ and $R^2$ form, together with the nitrogen atom to which they are attached, a morpholine ring or a pyrrolidine ring.

In an embodiment of the second aspect of the invention, compound (IV) is selected from 1-methyl-piperidine-4-carboxylic acid methoxy-methyl amide (IVa), 1-methyl-piperidine-4-carboxylic acid diethylamide (IVb), (1-methyl-piperidin-4-yl)-pyrrolidin-1-yl-methanone (IVc), and (1-methyl-piperidin-4-yl)-morpholin-4-yl-methanone (IVd), preferably 1-methyl-piperidine-4-carboxylic acid methoxy-methyl amide (IVa) or (1-methyl-piperidin-4-yl)-pyrrolidin-1-yl-methanone (IVc).

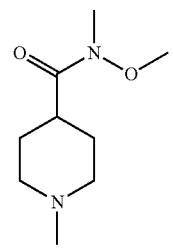
(IVa)

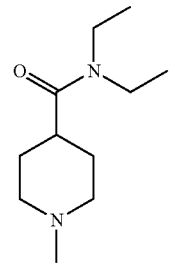
(IVb)

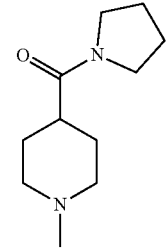
(IVc)

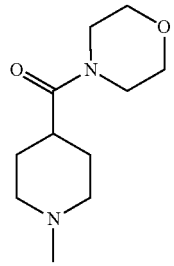
(IVd)

To obtain the compound of formula (V) or a salt thereof, a solution of N-(6-bromo-2-pyridyl)-2,2-dimethyl-propanamide (III) is prepared in a solvent such as anhydrous THF or anhydrous diethyl ether, preferably, anhydrous THF, and a solution of an organolithium compound, such as n-hexyllithium in a solvent such as hexane, is added to said solution under inert atmosphere (for example, $N_2$ atmosphere) and at a temperature comprised between −80 and −30° C., preferably about −70° C. The obtained mixture is kept under stirring for 10 to 60 minutes, preferably 30 minutes, at said temperature. The compound of formula (IVa) dissolved in a solvent, such as THF, is then added, maintaining a temperature of between −80 and −30° C., preferably about −60° C., and maintaining stirring at said temperature for 0.5 to 2 hours.

Alternatively, to obtain the compound of formula (V) or a salt thereof, a solution of N-(6-bromo-2-pyridyl)-2,2-dimethyl-propanamide (III) is prepared in a solvent such as anhydrous THF or anhydrous diethyl ether, preferably, anhydrous THF, and a solution of a first organolithium compound, such as phenyllithium in a solvent such as dibutyl ether, is added to said solution under inert atmosphere (for example, N₂ atmosphere) and at a temperature comprised between −80 and −30° C., preferably about −70° C. The obtained mixture is kept under stirring for 5 to 60 minutes, preferably between 5 to 45 minutes, at said temperature. Then, a second organolithium compound, such as n-hexyllithium in a solvent such as hexane, is added to said solution under inert atmosphere (for example, N₂ atmosphere) and at a temperature comprised between −80 and −30° C., preferably about −70° C. The obtained mixture is kept under stirring for 10 to 60 minutes, preferably 10 minutes, at said temperature. The compound of formula (IVa) dissolved in a solvent, such as THF, is then added, at a temperature between −5 and 0° C., and maintaining stirring at said temperature for 0.5 to 2 hours, preferably for 0.5 to 1 hour, more preferably for 0.5 hours.

After maintaining stirring, the reaction temperature is left to progress to a temperature comprised between −10 and 10° C., preferably about 0° C., and an aqueous solution of a base, such as a saturated aqueous solution of NH₄Cl, is added. The resulting mixture was neutralized to a pH comprised between 6 and 8, preferably about 7, by means of an aqueous solution of an acid, preferably a 2N hydrochloric acid solution. The two resulting phases are separated and the aqueous phase was extracted with several fractions of a sparingly water-miscible solvent such as methylene chloride. The combined organic phases are extracted with several fractions of an aqueous solution of an acid, such as an aqueous hydrochloric acid solution having a pH of about 2. The pH of the combined aqueous phases is modified to a value of between 11 and 13, preferably about 12, with an aqueous solution of 30% NaOH, and an extraction is performed with several fractions of a solvent, such as ethyl acetate, isopropyl acetate, or tert-butyl acetate, preferably ethyl acetate. The organic phase thus obtained is slowly cooled to a temperature comprised between −10 and 10° C., preferably about 0° C., the resulting solid being isolated by means of filtration. To facilitate precipitating the compound of formula (V), a co-solvent in which the compound is sparingly soluble, such as n-hexane or n-heptane, can be added.

The 1-methyl-piperidine-4-carboxylic acid amides of formula (IV) or the salts thereof can be obtained by converting 1-methyl-piperidine-4-carboxylic acid (VIII) into 1-methyl-piperidin-4-carbonyl chloride (IX) and the subsequent reaction with the one amine of formula NHR¹R², wherein R¹ and R² have the meanings described above.

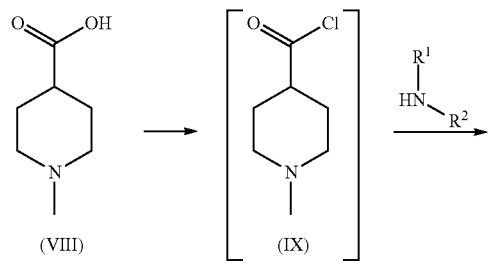

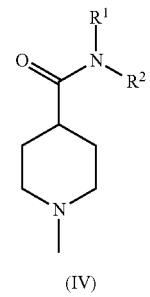

(IV)

In one embodiment, 1-methyl-piperidine-4-carboxylic acid (VIII) is mixed with a solvent, such as methylene chloride, and a chlorination agent, such as thionyl chloride, is added to said mixture at a temperature between 10 and 25° C., the mixture being heated at a temperature selected from 30 and 60° C., preferably between 35 and 55° C., more preferably between 45 and 50° C., for a time comprised between 1 and 6 hours, preferably between 3 and 5 hours. Optionally, the solvent is then eliminated by means of vacuum distillation. The hydrochloride, or the free base of the amine of formula NHR¹R² and a solvent such as methylene chloride are added to the obtained solid, or to the obtained reaction mixture. In case the amine of formula NHR¹R² is in liquid form, i.e. the free base of amine of formula NHR¹R² is a liquid, the addition of a solvent such as methylene chloride is optional, in case the elimination of the solvent by means of vacuum distillation of the preceding reaction is not carried out. The mixture is cooled at a temperature comprised between −5 and 10° C., preferably between −5 and 5° C., with a base such as triethylamine being slowly added and stirring being performed at a temperature comprised between −5 and 5° C., between 30 minutes and 2 hours, preferably about 1 hour. After eliminating the resulting salts by filtration and eliminating the solvent under vacuum, product (IV) is obtained.

Alternatively, after keeping under stirring at a temperature comprised between −5 and 5° C., between 30 minutes and 2 hours, preferably about 1 hour, an aqueous alkaline solution, such as 20% or 30% aqueous NaOH solution, can be added, with the obtained mixture being stirred at a temperature between 20 and 25° C., for a time comprised between 15 minutes and 1 hour, preferably for 30 minutes. The two resulting phases are separated and the aqueous phase was extracted with several fractions of a sparingly water-miscible solvent such as methylene chloride. The organic phases are combined, and the solvent eliminated by means of vacuum distillation, thereby obtaining product (IV). The obtained residue can be anhydrified by azeotropical distillation, by adding a suitable solvent, such as 2-methyltetrahydrofuran (2-THF), to said obtained residue.

In an embodiment of the second aspect of the invention, N-(6-bromo-pyridin-2-yl)-2,2-dimethyl-propionamide (III) is obtained by reacting 6-bromo-pyridin-2-ylamine (II) or the salts thereof with a pivaloylation agent selected from the group consisting of pivaloyl chloride, pivaloyl bromide, and pivalic acid anhydride, preferably pivaloyl chloride, in the presence of a base, selected from the group consisting of primary, secondary, or tertiary amines with one or more C₁-C₄-alkyl groups, preferably isopropylamine, triethylamine, or tert-butylamine, more preferably triethylamine.

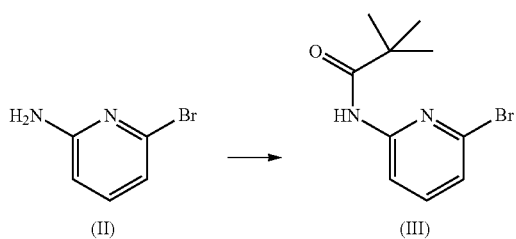

The reaction can be carried out by dissolving the compound of formula (II) in a solvent, such as dichloromethane, and adding to the solution the base, such as triethylamine, and the pivaloylation agent, such as pivaloyl chloride, at a temperature between 20 and 30° C., stirring for 2 to 7 hours. Optionally, after adding the pivaloylation agent, such as pivaloyl chloride, the obtained mixture can be heated to a temperature between 30 and 50° C., preferably to 40° C., and kept under stirring for 1 to 4 hours, preferably 2 hours.

In a third aspect, the present invention relates to a method of preparing lasmiditan (I) or a salt thereof (I•HX) comprising the steps of:
  a) preparing (6-amino-pyridin-2-yl)-(1-methyl-piperidin-4-yl)-methanone (VI) as described in the second aspect of the invention,
  b) reacting (6-amino-pyridin-2-yl)-(1-methyl-piperidin-4-yl)-methanone (VI) with a compound of formula (VII) under condensation conditions; and
  c) optionally reacting lasmiditan (I) with an acid to obtain the corresponding salt (I•HX).

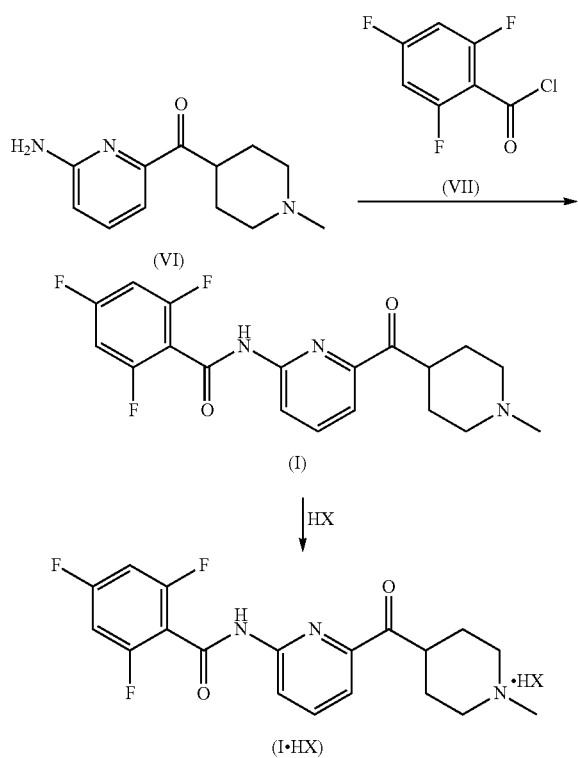

In a particular embodiment, step b) of condensation is performed by means of preparing a solution of (VII) in a solvent, such as toluene or THF, which is added at a temperature selected from −5 and 10° C., preferably about 0° C., to a previously prepared solution of (VI), and a base such as triethylamine in a solvent such as toluene or THF, with the temperature being maintained during the reaction between −5 and 10° C. for a time comprised between 20 minutes and 1 hour, preferably 40 minutes. Water is then added, with the resulting phases being separated and treating the aqueous phase with a sparingly water-miscible organic solvent, such as methylene chloride. The organic phases treated with an aqueous alkaline solution, such as an aqueous solution of $NaHCO_3$, are preserved. The solvent is eliminated from the obtained organic phase to obtain lasmiditan (I).

Alternatively, when water is added to the reaction mixture, after keeping under stirring, an aqueous alkaline solution, such as 1N aqueous solution of NaOH, can be further added until a pH comprised between 12 and 14, preferably 14, and the obtained mixture is stirred for a time comprised between 0.5 and 2 hours, preferably 1 hour, at a temperature between 20 and 25° C. The resulting phases are then separated, and the aqueous phase further treated with a sparingly water-miscible organic solvent, such as isopropyl acetate or methylene chloride. The combined organic phases are further treated with water, and the phases separated. The solvent is eliminated from the obtained organic phase by means of vacuum distillation to obtain lasmiditan (I).

Lasmiditan salts are addition salts with pharmaceutically acceptable acids that are typically formed by reacting a compound of formula (I) with an equimolar amount or excess of acid. Alternatively, hemi-salts can be formed by reacting a compound of formula (I) with the desired acid in a compound-to-acid ratio of 2:1. The inorganic acids commonly used for forming such salts include hydrochloric acid, hydrobromic acid, hydroiodic acid, sulfuric acid, phosphoric acid, and the like. The organic acids commonly used for forming such salts include p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are sulfate, pyrosulfate, bisulfate, sulfite, bisulfite, phosphate, monohydrogen phosphate, dihydrogen phosphate, metaphosphate, pyrophosphate, chloride, bromide, iodide, propionate acetate, decanoate, caprylate, acrylate, formate, heptanoate, propiolate, oxalate, malonate, succinate, hemisuccinate, suberate, sebacate, fumarate, maleate, butyne-1,4-dioate, 1-hexyne, 6-dioate, benzoate, chlorobenzoate, methylbenzoate, dinitrobenzoate, hydroxybenzoate, benzoate, benzoate, benzoate, benzoate, metobenzoate, hydroxybenoate, hydroxybenzoate, hydroxybenzoate, sulfonate, xylenesulfonate, phenylacetate, phenylpropionate, phenylbutyrate, citrate, lactate, p-hydroxybutyrate, glycolate, tartrate, methanesulfonate, propanesulfonate, naphthalene-1-sulfonate, naphthalene-2-sulfonate, mandelate. The preferred pharmaceutically acceptable salts are those formed with hydrochloric acid and succinic acid, preferably succinic acid.

In a fourth aspect, the present invention relates to the use of 2,2-dimethyl-N-[6-(1-methyl-piperidin-4-carbonyl)-pyridin-2-yl]-propionamide (V) in a method for preparing lasmiditan (I) or the salts thereof.

EXAMPLES

Example 1: Obtaining N-methoxy-N-methyl-1-methylpiperidyl-4-carboxamide (IVa)

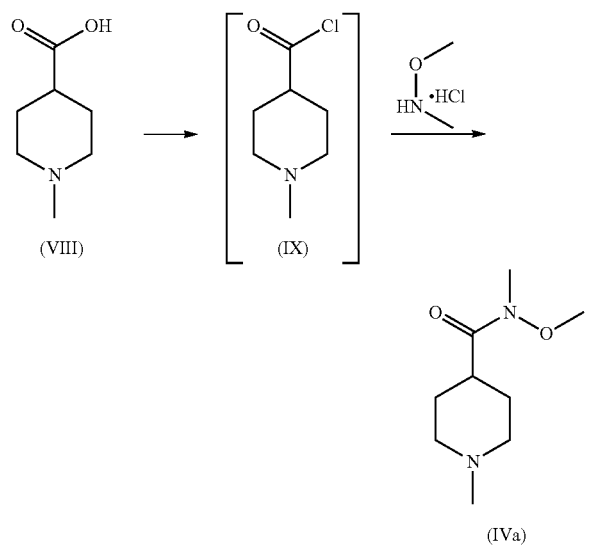

Figure 1:
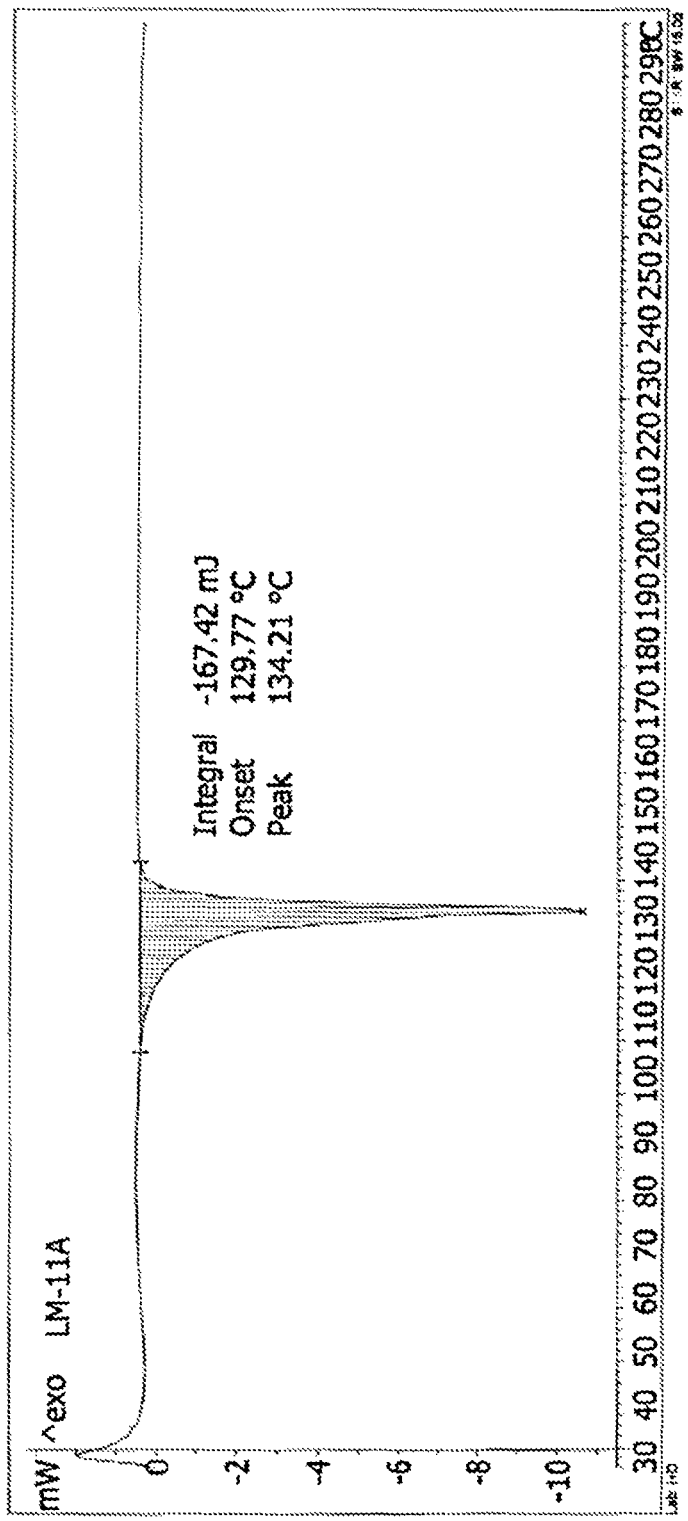
FIG. 1, shows the heat/temperature curve in a differential scanning calorimetry (DSC) obtained for 2,2-dimethyl-N-[6-(1-methylpiperidine-4-carbonyl)-2-pyridyl]propanamide (V).

20 g (139.7 mol) of 1-methylpiperidine-4-carboxylic acid (VIII) were mixed with 200 mL of methylene chloride and 18.3 g (154 mmol) of thionyl chloride were then added at a temperature of about 20° C. The resulting mixture was heated at the reflux temperature and kept under stirring at said temperature for 4 hours.

After keeping under stirring, the solvent was eliminated by means of vacuum distillation to obtain a white colored solid (IX). This was mixed two times with 50 mL of dichloromethane and the solvent was eliminated in both cases by means of vacuum distillation. 15 g (154 mmol) of N,O-dimethylhydroxylamine hydrochloride and 200 mL of methylene chloride were added to the solid thus obtained. The mixture thus obtained was cooled at a temperature of about 0° C. and 46.6 g (461 mmol) of triethylamine were slowly added. The resulting mixture was kept under stirring at a temperature of between 0 and 5° C. for 1 hour.

After keeping under stirring, the resulting salts were eliminated by means of filtration and the solvent was eliminated by means of vacuum distillation. 200 mL of toluene were added and the solvent was eliminated by means of vacuum distillation to obtain 19 g (yield: 73%) of a white solid corresponding to N-methoxy-N-methyl-1-methylpiperidyl-4-carboxamide (IVa).

Example 2: Obtaining (1-methyl-4-piperidyl)-pyrrolidin-1-yl-methanone (IVc)

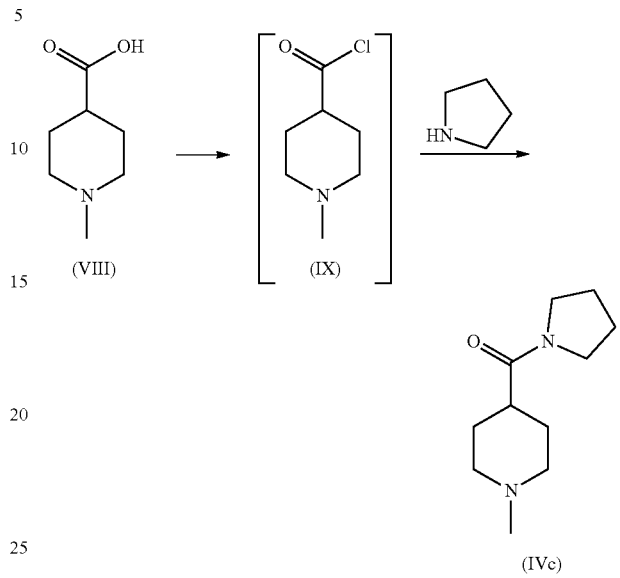

Procedure A: 10 g (70 mol) of 1-methylpiperidine-4-carboxylic acid (VIII) were mixed with 100 mL of tetrahydrofuran and 9.97 g (84 mmol) of thionyl chloride were then added at a temperature of about 20° C. The resulting mixture was heated at a temperature of between 45 and 50° C. and kept under stirring at said temperature for 2 hours.

After keeping under stirring, 9.94 g (140 mmol) of pyrrolidine were added. The mixture thus obtained was cooled at a temperature of between 5 and 10° C. and 21.2 g (231 mmol) of triethylamine were slowly added. The resulting mixture was kept under stirring at a temperature of about 20° C. for 1 hour.

After keeping under stirring, 25 mL of an aqueous solution of 30% NaOH and 12 mL of water were slowly added at a temperature of about 25° C. The aqueous phase was separated and successively treated with two fractions of 100 mL of tetrahydrofuran. The organic phases were combined and the solvent was eliminated by means of vacuum distillation. 100 mL of toluene were added and the solvent was eliminated by means of vacuum distillation to obtain 9.6 g (yield: 70%) of a white solid corresponding to (1-methyl-4-piperidyl)-pyrrolidin-1-yl-methanone (IVc).

If necessary, the product thus obtained can be purified by means of dissolving in 5 volumes of cyclohexane for every gram of product, heating under reflux, and then slowly cooling the resulting solution to a temperature of about 20° C. The white solid thus obtained is filtered and dried at a temperature of between 40 and 50° C. The purification commonly yields 80-85%.

Procedure B: 50 g (349 mmol) of 1-methylpiperidine-4-carboxylic acid (VII) were suspended in 500 mL of methylene chloride, and 45.7 g (384 mmol) of thionyl chloride were then added at a temperature of about 20° C. The resulting mixture was heated to a temperature between about 45 and 50° C. and kept under stirring at said temperature for 2 hours.

After keeping under stirring, 27.3 g (384 mmol) of pyrrolidine were added. The mixture thus obtained was cooled to a temperature of between 0 and 10° C., and 97.2 g (960 mmol) of triethylamine were slowly added during 1 h. The resulting thick suspension was stirred for 1 hour at a temperature between about 0 and 5° C.

After keeping under stirring, 347 mL of a 20% aqueous solution of NaOH were added and the mixture was stirred for 30 minutes at a temperature of between 20 and 25° C. The aqueous phase was separated and extracted twice with 200 mL of methylene chloride. The organic phases were combined and the solvent was eliminated by means of vacuum distillation to obtain 58.2 g of a solid residue (yield: 85%, water content (Karl-Fisher method)=0.40%). The resulting residue was anhydrified by azeotropical distillation in 200 mL of 2-methyl-tetrahydrofurane (water content %<0.1%).

Procedure C: 100 g (557 mmol) of the hydrochloride salt of 1-methylpiperidine-4-carboxylic acid (VII-HCl) were suspended in 500 mL of methylene chloride, and 79.47 g (668 mmol) of thionyl chloride were slowly added at a temperature of about 20° C. The resulting mixture was heated to a temperature between about 45 and 50° C. and kept under stirring at said temperature for 2 hours.

After keeping under stirring, 43.55 g (612 mmol) of pyrrolidine were added. The obtained mixture was cooled to a temperature of between 0 and 10° C. and 229.8 g (2.271 mol) of triethylamine were slowly added during 3 h. The resulting thick suspension was stirred for 1 hour at a temperature between about 0 and 10° C.

After keeping under stirring, 371 g of a 30% aqueous solution of NaOH were added and the mixture was stirred for 30 minutes at a temperature of between 20 and 25° C. The aqueous phase was separated and extracted twice with 200 mL of methylene chloride. The organic phases were combined and the solvent was eliminated by means of vacuum distillation to obtain 96.0 g of a solid residue (yield: 88%; water content (Karl-Fisher method)=0.31%). The resulting residue was anhydrified by azeotropical distillation in 325 mL of 2-methyl-tetrahydrofurane (water content %<0.1%).

Example 3: Obtaining N-(6-bromo-2-pyridyl)-2,2-dimethyl-propanamide (III)

and a fraction of a saturated aqueous solution of NaHCO₃, in this order. The solvent of the obtained organic solution was eliminated by means of distillation and the resulting solid was mixed with 40 mL of n-heptane. Heating under reflux was performed and the resulting solution was then slowly cooled to a temperature of about 5° C. 22.6 g (yield: 76.1%) of a white crystalline solid corresponding to N-(6-bromo-2-pyridyl)-2,2-dimethyl-propanamide (III) were obtained by means of filtration.

Procedure B: 49 g (283 mmol) of 6-bromopyridin-2-amine (II) and 41.27 g (408 mmol) of triethylamine, were dissolved in 147 mL of methylene chloride at a temperature of about 20° C. 40.98 g (340 mmol) of 2,2-dimethylpropionil chloride (pivaloyl chloride) were then added at a temperature of about 20° C. The resulting mixture was heated to temperature of about 40° C., and kept under stirring for 2 hours.

After keeping under stirring, 147 mL of water were cautiously added to the mixture, and the pH was adjusted to a value between 1 and 2 with a 1N aqueous solution of HCl. The mixture was stirred for 30 minutes at a temperature of between 20 and 25° C. The phases were separated and the aqueous layer was extracted with 98 mL of dichloromethane. The combined organic extracts was washed twice with an 8% aqueous solution of NaHCO₃ (73 mL) and further with 73 mL of water. The solvent was eliminated by means of vacuum distillation, to obtain an oily residue.

The resulting oily residue was dissolved in 73 mL of n-heptane by heating at a temperature of about 80° C. The obtained solution was cooled to a temperature between about 60 and 65° C. and was maintained under stirring for 1 hour to obtain a thick suspension. The resultant suspension was slowly cooled to a temperature of about 0° C., and it was stirred for 2 hours at said temperature. The obtained solid was filtered and dried at a temperature of 50° C. to obtain 66.9 g (yield: 92.0%; purity by means of UHPLC: 99.5%) of a white-pale yellow crystalline solid corresponding to N-(6-bromo-2-pyridyl)-2,2-dimethyl-propanamide (III).

¹H-NMR (CDCl₃, 400 MHz) δ(ppm): 8.21 (1H, dd), 7.98 (1H, s), 7.54 (1H, ddd), 7.19 (1H, dd), 1.28 (9H, s)

¹³C-NMR (CDCl₃, 400 MHz) δ(ppm): 177.09, 151.67, 140.57, 139.07, 123.39, 112.25, 39.88, 27.37

Example 4: Obtaining 2,2-dimethyl-N-[6(1-methylpiperidin-4-carbonyl)-2-pyridyl]propanamide (V)

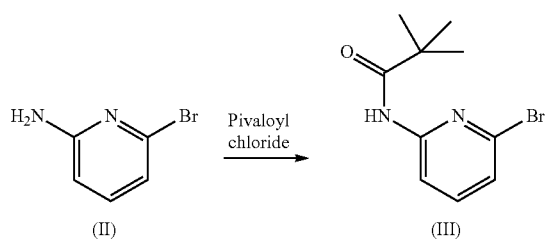

Procedure A: 20 g (0.12 mol) of 6-bromopyridin-2-amine (II) were dissolved in 200 mL of dichloromethane at a temperature of 25° C. 48.7 mL (35.3 g, 0.35 mol) of triethylamine and 21.8 mL (21.3 g, 0.18 mol) of 2,2-dimethylpropionyl chloride (pivaloyl chloride) were slowly added, in this order, at a temperature of about 25° C. The reaction was kept under stirring at said temperature for 5 hours.

After keeping under stirring, the resulting white solid was eliminated by means of filtration and the solvent was evaporated by means of distillation to obtain a residue which was dissolved in ethyl acetate. The resulting solution was washed with a fraction of a 1N aqueous hydrochloric acid solution

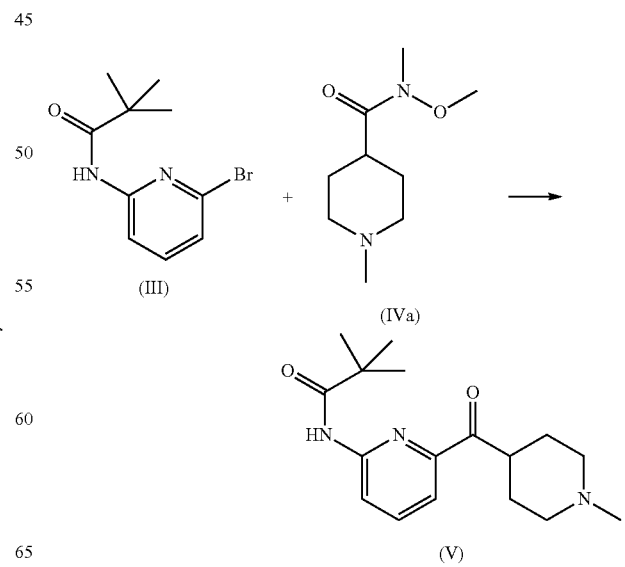

7.1 mL of a 2.3 M n-hexyllithium solution in hexane (16.3 mmol) were added to a solution previously prepared from 2 g (7.8 mmol) of N-(6-bromo-2-pyridyl)-2,2-dimethyl-propanamide (III) in 5 mL of anhydrous THF under inert $N_2$ atmosphere and at a temperature of about −70° C. The obtained mixture was kept under stirring for 30 minutes at said temperature. 2.3 g (12.3 mmol) of N-methoxy-N-methyl-1-methylpiperdyl-4-carboxamide (IVa) dissolved in 9.2 mL of THF were then added, maintaining the temperature of about −60° C. and the resulting reaction mixture was kept under stirring at said temperature for 1 hour.

After keeping under stirring, the reaction temperature was left to progress to 0° C. and 2.9 mL of a saturated aqueous solution of $NH_4Cl$ were added. The resulting mixture was neutralized to a pH of about 7 by means of a 2N aqueous hydrochloric acid solution. The two resulting phases were separated and the aqueous phase was extracted with 3 fractions of 10 mL of methylene chloride each. The combined organic phases were extracted with 3 fractions of an aqueous hydrochloric acid solution having a pH of about 2. The pH of the combined aqueous phases was modified to about a value of 12 with an aqueous solution of 30% NaOH and extraction was performed with two fractions of 10 mL of ethyl acetate each. The organic phase thus obtained was slowly cooled to a temperature of about 0° C. The resulting solid was isolated by means of filtration to obtain 1.89 g (yield: 80%, purity by means of UHPLC: 98.95%) of a white solid corresponding to 2,2-dimethyl-N-[6-(1-methylpiperidin-4-carbonyl)-2-pyridyl]propanamide (V).

$^1$H-NMR (CDCl$_3$, 400 MHz) δ(ppm): 8.42 (1H, dd), 8.00 (1H, s), 7.82 (1H, m), 7.72 (1H, dd), 3.67 (1H, m), 2.92-2.84 (4H, m), 2.31 (3H, s), 2.11 (1H, m), 1.94 (1H, m), 1.85 (1H, m), 1.68 (1H, m), 1.39 (9H, s)

$^{13}$C-NMR (CDCl$_3$, 400 MHz) δ(ppm): 213.13, 203.09, 177.19, 150.98, 139.27, 118.43, 117.39, 55.22, 46.36, 41.44, 40.31, 28-27 (3C), 22.47

Example 5: Obtaining 2,2-dimethyl-N-[6(1-methylpiperidin-4-carbonyl)-2-pyridyl]propanamide (V)

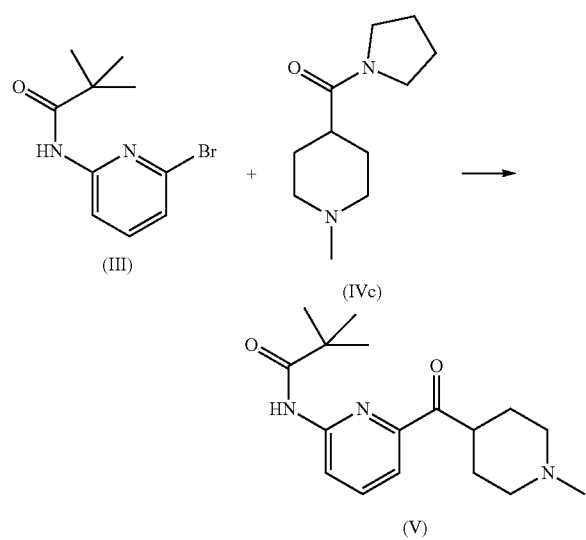

Procedure A: 7.1 mL of a 2.3 M n-hexyllithium solution in hexane (16.3 mmol) were added to a solution previously prepared from 3 g (11.7 mmol) of N-(6-bromo-2-pyridyl)-2,2-dimethyl-propanamide in 5 mL of THF under inert $N_2$ atmosphere and at a temperature of about −70° C. The obtained mixture was kept under stirring for 15 minutes at said temperature. 3.1 g (15.8 mmol) of (1-methyl-piperidin-4-yl)-pyrrolidin-1-yl-methanone (IVc) dissolved in 12.4 mL of THF were then added, maintaining the temperature of about −70° C. and the resulting reaction mixture was kept under stirring at said temperature for 30 minutes.

After keeping under stirring, the reaction temperature is left to progress to 0° C. and 4.3 mL of a saturated aqueous solution of $NH_4Cl$ were added. The resulting mixture was neutralized to a pH of about 7 by means of a 2N aqueous hydrochloric acid solution. The two resulting phases were separated and the aqueous phase was extracted with 3 fractions of 10 mL of methylene chloride each. The combined organic phases were treated with acetic acid and three extractions were performed with fractions of 12 mL of water each. The pH of the combined aqueous phases was modified to about a value of 12 with an aqueous solution of 30% NaOH and two extractions were performed with fractions of 10 mL of ethyl acetate each. The combined organic phases were slowly cooled to a temperature of about 0° C. The resulting solid was isolated by means of filtration to obtain 2.81 g (yield: 79.1%, purity by means of UHPLC: 99.05%) of a white solid corresponding to 2,2-dimethyl-N-[6-(1-methylpiperidin-4-carbonyl)-2-pyridyl]propanamide (V).

Procedure B: 120.8 mL of a 1.9 M solution of phenyllithium in dibutyl ether (229 mmol) were added dropwise to previously prepared solution of 59 g of N-(6-bromo-2-pyridyl)-2,2-dimethyl-propanamide (229.5 mmol) in 413 mL of THF under inert $N_2$ atmosphere at a temperature of about −70° C. The obtained mixture was stirred for 5-10 minutes at said temperature. Then, 99.8 mL of a 2.3 M solution of n-hexyllithium in hexane (229 mmol) were added dropwise at a temperature of about −70° C. (maintaining the internal temperature between −70° C. and −60° C. during the addition). The resulting mixture was stirred for about 10 minutes at said temperature, after which time the resulting mixture was added to a solution of 49.5 g (252 mmol) of 1-methyl-piperidin-4-yl)-pyrrolidin-4-yl-methanone (IVc) in 198 mL of THF at a temperature of between 0 and −5° C. and the obtained mixture was stirred for about 30 minutes.

After keeping under stirring, 84.3 mL of a 10% aqueous solution of $NH_4Cl$ was added at 0° C. and the mixture was neutralized (pH of 7.4) by the addition of an aqueous 2N solution of HCl. Then, 99 mL of ethyl acetate were added and the phases were separated. The aqueous layer was extracted twice with ethyl acetate (2×99 mL). The organic layers were combined and AcOH 90% was added to a value of pH of about 4. The two phases were separated, and the organic layer was extracted twice with water (2×99 mL). The resulting aqueous phase was basified to a pH of about 10 with a 50% aqueous solution of $K_2CO_3$ and extracted twice with isopropyl acetate (2×99 mL). The combined organic phases were slowly cooled to a temperature of about 0° C. The resulting solid was filtered and dried at a temperature of about 50° C. to obtain 66.2 g (yield: 89.0%, purity by means of UHPLC: 99.3%) of a yellowish crystalline solid corresponding to 2,2-dimethyl-N-[6-(1-methylpiperidine-4-carbonyl)-2-pyridyl]propanamide (V).

Example 6: Obtaining (6-amino-2-pyridyl)-(1-methyl-4-piperidyl)methanone (VI)

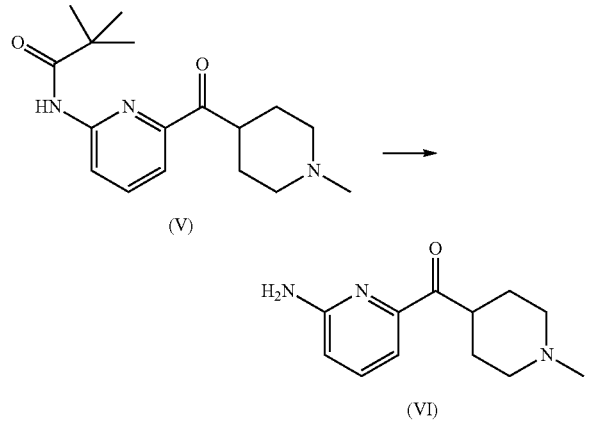

Procedure A: 0.9 g (3 mmol) of 2,2-dimethyl-N-[6-(1-methylpiperidin-4-carbonyl)-2-pyridyl]propanamide (V) were dissolved in 59 mL of water. 2.97 mL of concentrated hydrochloric acid were added to the solution thus obtained and the mixture was kept under stirring for 3 hours at the reflux temperature.

After keeping under stirring, a saturated aqueous solution of NaHCO$_3$ was added until a pH of about 8 and extraction was performed with three fractions of 10 mL of ethyl acetate each. The solvent of the combined organic phases was eliminated by means of distillation to obtain a residue comprising (6-amino-2-pyridyl)-(1-methyl-4-piperidyl)methanone (VI) (0.65 g, with purity by means of UPLC of 91.6%) which is used without further purification in the next reaction.

Procedure B: 44.0 g (150 mmol) of 2,2-dimethyl-N-[6-(1-methylpiperidine-4-carbonyl)-2-pyridyl]propanamide (V) were dissolved in 176 mL of water. 25.4 mL of concentrated hydrochloric acid were added to the solution thus obtained and the mixture was kept under stirring for 3 h at the reflux temperature.

After keeping under stirring, a 30% aqueous solution of NaOH was added until a pH of about 12. The aqueous phase was extracted three times with three fractions of 150 mL of ethyl acetate each. The solvent of the combined organic phases was eliminated by means of vacuum distillation, to obtain a residue comprising (6-amino-2-pyridyl)-(1-methyl-4-piperidyl)methanone (VI) (31.2 g, purity by means of UHPLC: 98.0%), which was used without further purification in the next reaction.

Example 7: Obtaining 2,4,6-trifluoro-N-[6-(1-methyl-4-piperidyl-carbonyl)-2-pyridyl]benzamide (lasmiditan) (I)

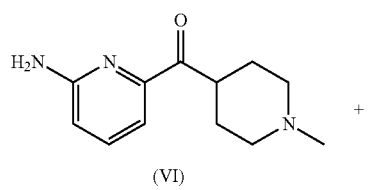

+

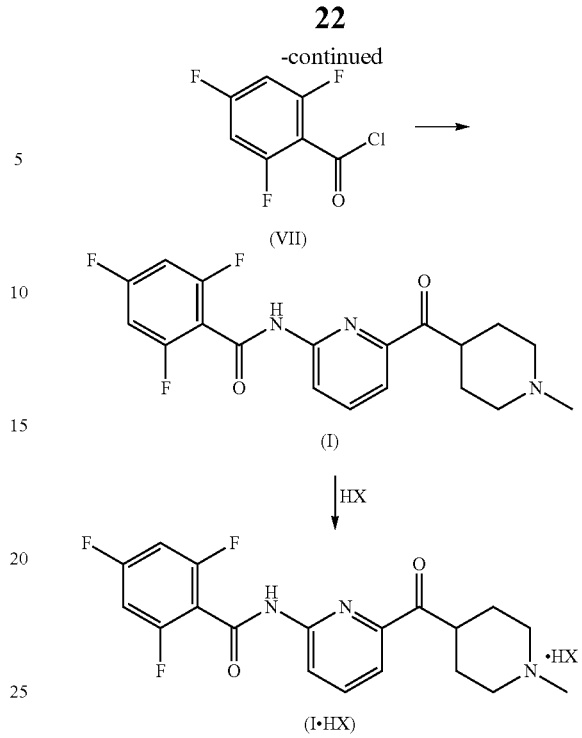

Procedure A: A previously prepared solution in toluene of 2,4,6-trifluorobenzyl acid chloride (VII) (1.55 g, 7.95 mmol) was added at a temperature of about 0° C. to a previously prepared solution containing 1.284 g of 6-amino-2-pyridyl)-(1-methyl-4-piperidyl)methanone (VI) (purity by means of UHPLC of 91.1%, equivalent to 1.169 g, 5.33 mmol) and 2.23 mL of triethylamine (15.99 mmol) in 10 mL of toluene. The resulting mixture was kept at a temperature of about 0° C. for 40 minutes.

After keeping at said temperature, 15 mL of water were added and the phases were separated. The aqueous phase thus obtained was successively treated with two fractions of 10 mL of methylene chloride each. The organic phases were combined and treated with 10 mL of a saturated aqueous solution of NaHCO$_3$. The solvent of the organic phase thus obtained was eliminated to produce 1.7 g (yield 85%, purity by means of UHPLC: 98.91%) of 2,4,6-trifluoro-N-[6-(1-methyl-4-piperidyl-carbonyl)-2-pyridyl]benzamide (I).

Procedure B: A previously prepared solution in THF (153 mL) of 2,4,6-trifluorobenzoyl chloride (51.0 g, 262.7 mmol), was slowly added at a temperature of about 0° C. to a previously prepared solution containing 48.0 g (218.9 mmol) of (6-amino-2-pyridyl)-(1-methyl-4-piperidiyl)-methanone (VI) and 39.9 g (394 mmol) of triethylamine in 240 mL of THF. The resulting mixture was kept at a temperature of about 0° C. for 40 minutes.

After keeping at said temperature, 350 mL of water were added and a 1N aqueous solution of NaOH was added until a pH of about 14. The resulting mixture was stirred for 1 hour. The organic phase was separated and the aqueous phase was extracted twice with isopropyl acetate. The combined organic phases were consecutively washed with three fractions of 250 mL of water. The solvent of the organic phase thus obtained was removed by means of vacuum distillation to obtain 79.3 g (purity by means of UHPLC: 96.8%) of an oily residue comprising 2,4,6-trifluoro-N-[6-(1-methyl-4-piperidyl-carbonyl)-2-piridyl]benzamide.

$^1$H-NMR (CDCl$_3$, 400 MHz) δ(ppm): 8.51 (1H, dd), 8.44 (1H, s), 7.92 (1H, m), 7.81 (1H, dd), 6.84-6.79 (2H, m), 3.64-3.57 (1H, m), 2.93-2.89 (2H, m), 2.30 (3H, s), 2.14-2.06 (2H, m), 1.89-1.84 (4H, m)

Example 8: Obtaining the hemosuccinate salt of 2,4,6-trifluoro-N-[6-(1-methyl-4-piperidyl-carbonyl)-2-pyridyl]benzamide (lasmiditan) (I•½ Hemisuccinate)

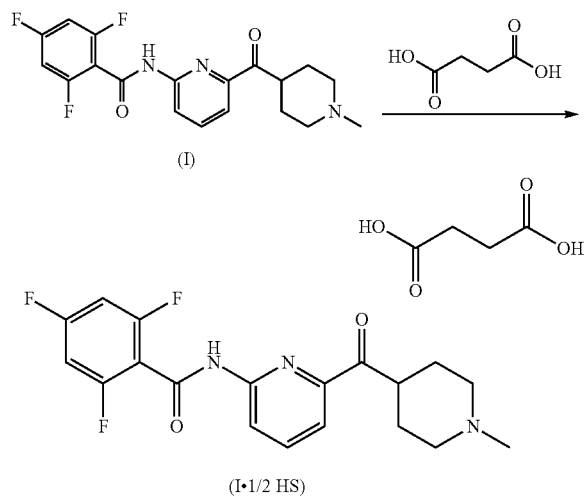

44.8 g (114 mmol) of the oily residue comprising 2,4,6-trifluoro-N-[6-(1-methyl-4-piperidyl-carbonyl)-2-piidyl] benzamide (I) obtained according to Example 7 were solved in 172 mL of ethanol. The solution was heated to a temperature between about 78 and 80° C. and filtered. 7.43 g (63 mmol) of succinic acid were solved in 134 mL of ethanol at a temperature of about 25° C. and the resulting solution was filtered. The solution containing succinic acid was added to the solution of 2,4,6-trifluoro-N-[6-(1-methyl-4-piperidyl-carbonyl)-2-piridyl]benzamide (I) maintaining the temperature of the mixture between about 76 and 78° C. After the addition, the temperature was cooled to about 70° C. and the mixture was stirred at this temperature for 4 hours (crystallization started at this temperature). The mixture was slowly cooled to a temperature of about 20° C. and it was stirred overnight. After stirring overnight, the solid was filtered and dried at a temperature of about 50° C. to obtain 39.0 g (yield: 78.2%, purity by means of UHPLC: 99.4%) of hemisuccinate salt of 2,4,6-trifluoro-N-[6-(1-methyl-4-piperidyl-carbonyl)-2-piridyl]benzamide (I•½ Hemisuccinate, hemisuccinate salt of lasmiditan).

Figure 2:
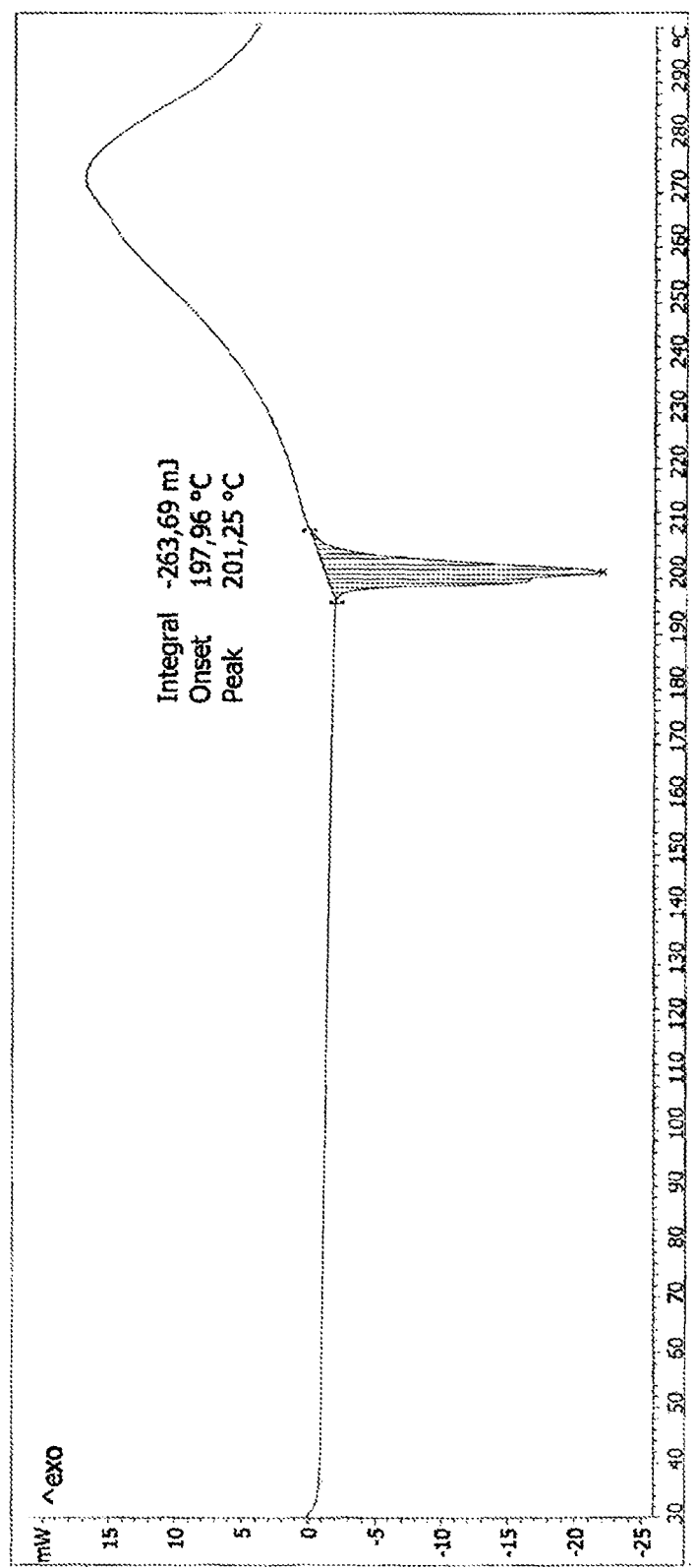
FIG. 2 shows the heat/temperature curve in a differential scanning calorimetry (DSC) obtained for the hemisuccinate salt of 2,4,6-trifluoro-N-[6-(1-methyl-4-piperidyl-carbonyl)-2-piridyl]benzamide (hemisuccinate salt of lasmiditan) (I•½ Hemisuccinate).
Figure 3:
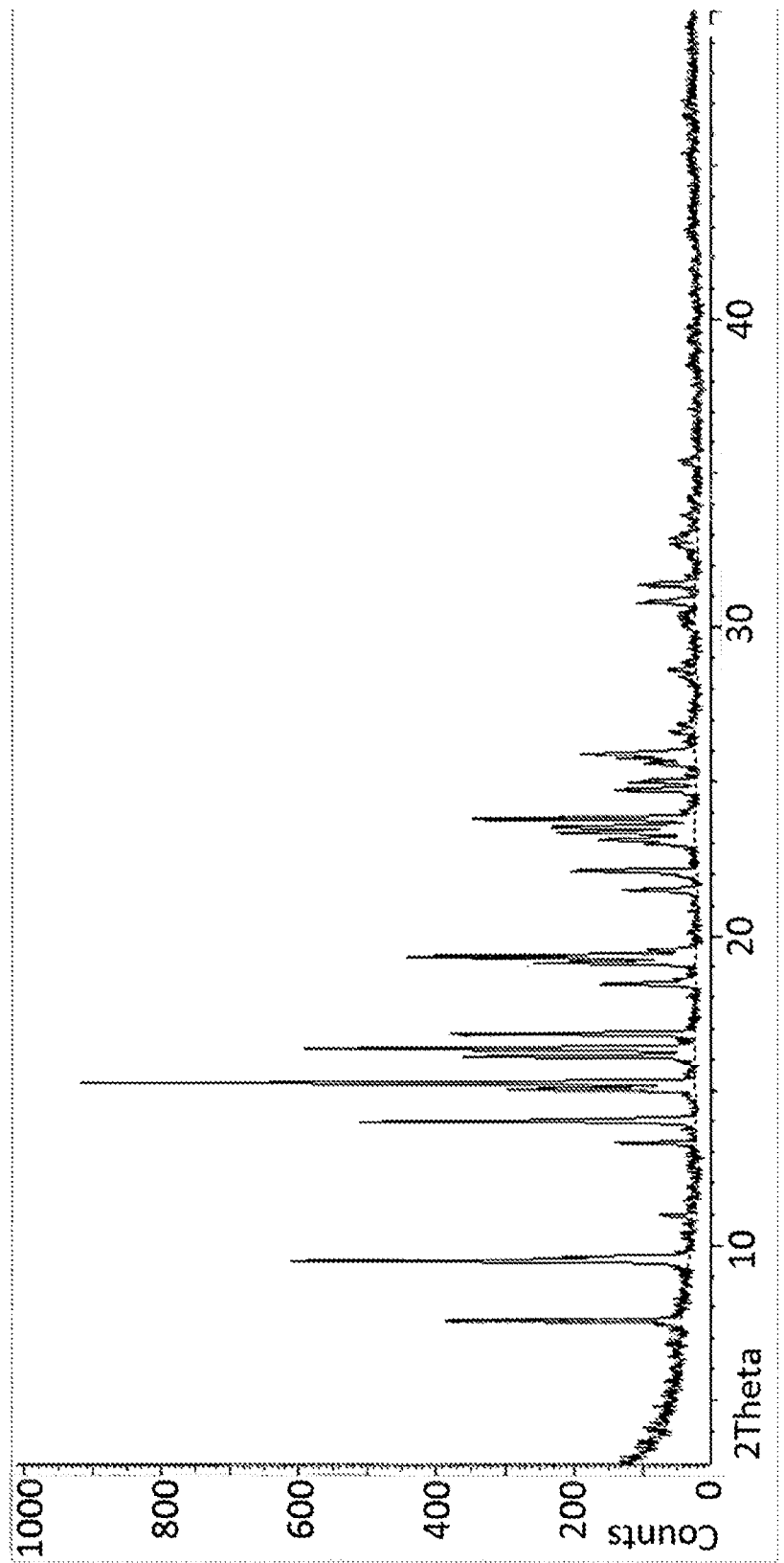
FIG. 3 shows the X-ray powder diffractogram (XRPD) obtained for the hemisuccinate salt of 2,4,6-trifluoro-N-[6-(1-methyl-4-piperidyl-carbonyl)-2-piridyl]benzamide (hemisuccinate salt of lasmiditan) (I•½ Hemisuccinate).

FIGS. 2 and 3, respectively show the DSC and XRPD spectra of compound I•½ Hemisuccinate. Both results coincide with the differential scanning calorimetry and X-ray powder diffractogram results for the crystalline form A, which was disclosed in the application WO 2011/123654 A1

The $^1$H and $^{13}$C NMR spectra were acquired in a 400 MHz Brucker Avance III spectrometer.

DSC analysis was performed in a Mettler Toledo 822e apparatus with STARe SW15 software. Parameters: heating range of 30 to 300° C. with a ramp of 20° C./min and $N_2$ flow of 60 mL/min. The measurement was taken with a perforated closed capsule.

XRPD analysis was performed using a BRUKER D2 PHASER model X-ray powder diffractometer equipped with a copper anode using Cu Kα radiation (1.54060 Å). Scanning parameters: 3-50 degrees 2θ, continuous scan, ratio: 5.6 degrees/minute.

UHPLC Method:

The purity of the obtained products was analyzed by means of the ultra-high-performance liquid chromatography technique in a Waters Acquity model apparatus, provided with a photodiode detector and thermostatted oven for the column. A BEH Shield C18 column (2.1×100 mm and 1.8 μm) and mobile phases A (10 mM ammonium bicarbonate, pH 10), B (acetonitrile), and C (water) were used with the following analysis conditions:

Flow rate: (mL/min): 0.3
Column temperature (° C.): 40
Wavelength (nm): 225
Inj. vol. (μL): 1
Acquisition time (min): 10
Diluent: acetonitrile/water (7:3)
Gradient:

| t (min) | % A | % B | % C |
|---|---|---|---|
| 0 | 5 | 5 | 90 |
| 1 | 5 | 5 | 90 |
| 6 | 5 | 85 | 10 |
| 8 | 5 | 85 | 10 |
| 9 | 5 | 5 | 90 |
| 12 | 5 | 5 | 90 |

The invention claimed is:

1. 2,2-dimethyl-N-[6-(1-methyl-piperidin-4-carbonyl)-pyridin-2-yl]-propionamide (compound V) or a salt thereof

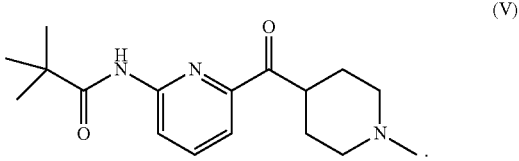 [SMILES: CN1CCC(C(=O)c2cccc(NC(=O)C(C)(C)C)n2)CC1]

2. The compound according to claim 1, characterized by presenting a heat/temperature curve in a differential scanning calorimetry (DSC) having a negative peak at a temperature comprised between 125 and 140° C.

3. A method of preparing (6-amino-pyridin-2-yl)-(1-methyl-piperidin-4-yl)-methanone (compound VI) or a salt thereof which comprises reacting 2,2-dimethyl-N-[6-(1-methyl-piperidin-4-carbonyl)-pyridin-2-yl]-propionamide (compound V) or a salt of said compound with an acid

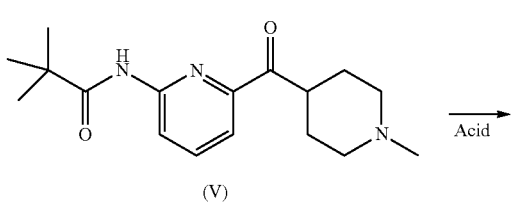

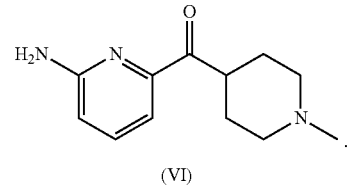

4. The method according to claim 3, wherein the acid is hydrochloric acid.

5. The method according to claim 3, wherein the 2,2-dimethyl-N-[6-(1-methyl-piperidin-4-carbonyl)-pyridin-2-yl]-propionamide (compound V) is obtained by reacting N-(6-bromo-pyridin-2-yl)-2,2-dimethyl-propionamide (compound III) with a 1-methyl-piperidine-4-carboxylic acid amide of compound (IV) or the salts thereof, wherein $R^1$ is selected from the group consisting of $C_1$-$C_3$ alkyl and $C_1$-$C_3$ alkoxy, and $R^2$ is selected from the group consisting of $C_1$-$C_3$ alkyl, or wherein $R^1$ and $R^2$ form, together with the nitrogen atom to which they are attached, a 5 to 6-membered heterocycle which may further comprise an oxygen atom, in the presence of an organolithium compound, and if a salt (compound V·HX) of compound (V) is to be obtained, reacting the obtained product with the corresponding acid

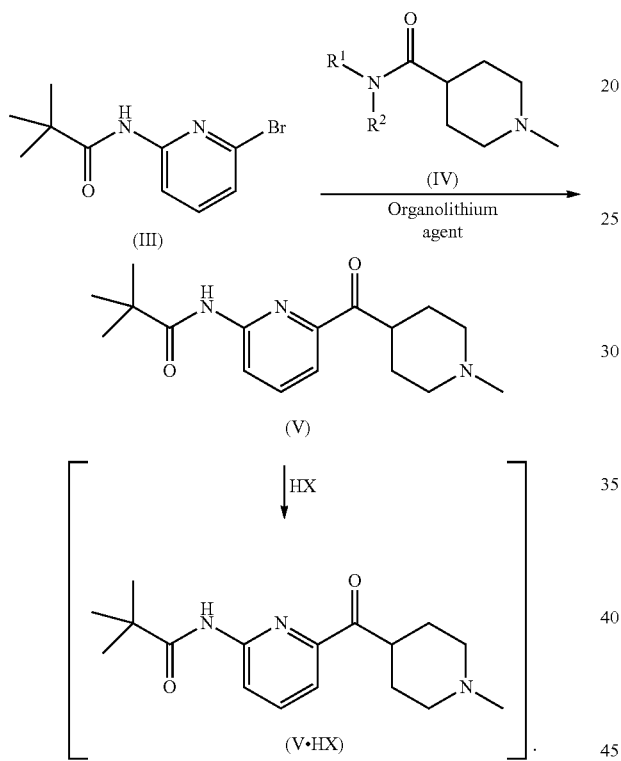

6. The method according to claim 5, wherein $R^1$ is selected from the group consisting of methyl and ethyl, and $R^2$ is selected from the group consisting of methoxy and ethyl, or wherein $R^1$ and $R^2$ form, together with the nitrogen atom to which they are attached, a morpholine ring or a pyrrolidine ring.

7. The method according to claim 5, wherein the compound (compound IV) is selected from the group consisting of 1-methyl-piperidine-4-carboxylic acid diethylamide (compound IVb), 1-methyl-piperidine-4-carboxylic acid methoxy-methyl amide (compound IVa), (1-methyl-piperidin-4-yl)-pyrrolidin-1-yl-methanone (compound IVc), and (1-methyl-piperidin-4-yl)-morpholin-4-yl-methanone (compound IVd).

8. The method according to claim 7, wherein the compound (compound IV) is 1-methyl-piperidine-4-carboxylic acid methoxy-methyl amide (compound IVa).

9. The method according to claim 7, wherein the compound (compound IV) is (1-methyl-piperidin-4-yl)-pyrrolidin-1-yl-methanone (compound IVc).

10. The method according to claim 5, wherein the organolithium agent is selected from the group consisting of n-hexyllithium, n-butyllithium, phenyllithium, and mixtures thereof.

11. The method according to claim 5, wherein N-(6-bromo-pyridin-2-yl)-2,2-dimethyl-propionamide (compound III) is obtained by reacting 6-bromo-pyridin-2-ylamine (compound II) or the salts thereof with a pivaloylation agent selected from the group consisting of pivaloyl chloride, pivaloyl bromide, and pivalic acid anhydride in the presence of a base

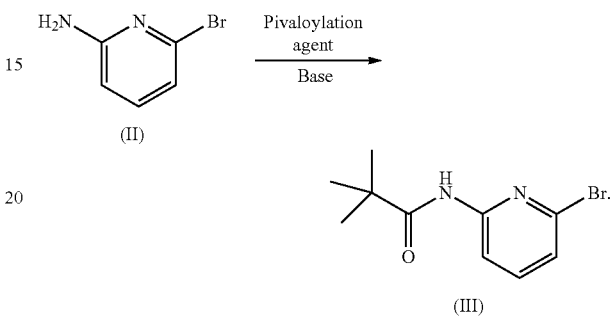

12. The method according to claim 11, wherein the pivaloylation agent is pivaloyl chloride.

13. The method according to claim 11, wherein the base is triethylamine.

14. A method of preparing lasmiditan (compound I) or a salt thereof (compound I·HX) comprising the steps of:
 a) preparing (6-amino-pyridin-2-yl)-(1-methyl-piperidin-4-yl)-methanone (compound VI) as described in claim 3,
 b) reacting (6-amino-pyridin-2-yl)-(1-methyl-piperidin-4-yl)-methanone (compound VI) with a compound of compound (VII) under condensation conditions; and
 c) optionally reacting lasmiditan (compound I) with an acid to obtain the corresponding salt (compound I·HX)

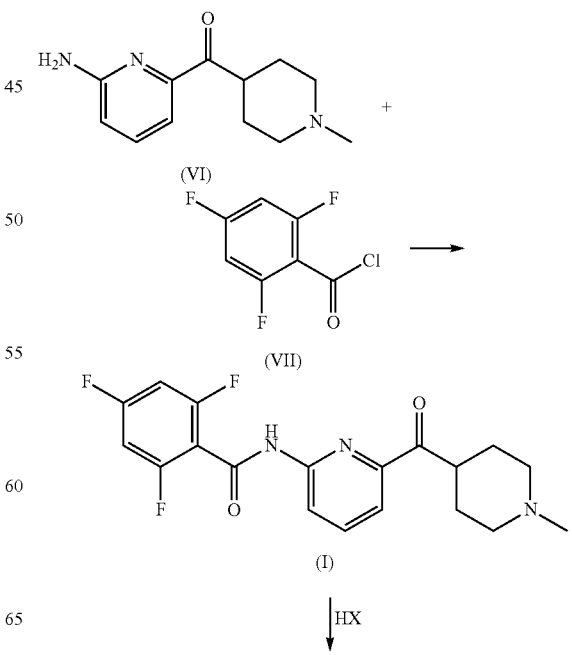

-continued
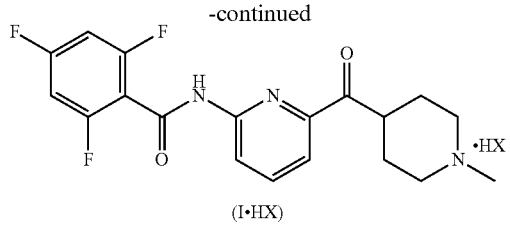
(I·HX)
* * * * *